United States Patent
Joo et al.

(10) Patent No.: US 10,696,611 B2
(45) Date of Patent: Jun. 30, 2020

(54) ADAMANTANE DERIVATIVE COMPOUND

(71) Applicant: AMOREPACIFIC CORPORATION, Seoul (KR)

(72) Inventors: Yung Hyup Joo, Yongin-si (KR); Song Seok Shin, Yongin-si (KR); Byoung Young Woo, Yongin-si (KR); Heung Soo Baek, Yongin-si (KR); Yong Deog Hong, Yongin-si (KR); Hong-Ju Shin, Yongin-si (KR); Yeon Su Jeong, Yongin-si (KR); Jon Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/506,972

(22) PCT Filed: Aug. 24, 2015

(86) PCT No.: PCT/KR2015/008816
§ 371 (c)(1),
(2) Date: Feb. 27, 2017

(87) PCT Pub. No.: WO2016/032182
PCT Pub. Date: Mar. 3, 2016

(65) Prior Publication Data
US 2017/0283347 A1    Oct. 5, 2017

(30) Foreign Application Priority Data

Aug. 29, 2014  (KR) .................. 10-2014-0113975
Jul. 31, 2015   (KR) .................. 10-2015-0108849

(51) Int. Cl.
| | | |
|---|---|---|
| *C07C 239/00* | (2006.01) |
| *C07D 453/02* | (2006.01) |
| *C07D 413/00* | (2006.01) |
| *A61K 31/16* | (2006.01) |
| *C07C 13/615* | (2006.01) |
| *C07C 233/59* | (2006.01) |
| *A61K 31/167* | (2006.01) |
| *A61K 8/42* | (2006.01) |
| *C07C 233/60* | (2006.01) |
| *A61K 8/49* | (2006.01) |
| *A61Q 7/00* | (2006.01) |
| *A61K 31/166* | (2006.01) |
| *C07C 233/63* | (2006.01) |
| *C07C 231/02* | (2006.01) |
| *C07C 233/58* | (2006.01) |
| *C07C 265/12* | (2006.01) |
| *A61Q 19/00* | (2006.01) |
| *C07D 263/56* | (2006.01) |
| *C07C 15/04* | (2006.01) |
| *C07C 233/57* | (2006.01) |
| *A61K 31/4184* | (2006.01) |

(52) U.S. Cl.
CPC .............. *C07C 13/615* (2013.01); *A61K 8/42* (2013.01); *A61K 8/49* (2013.01); *A61K 8/4973* (2013.01); *A61K 31/166* (2013.01); *A61K 31/167* (2013.01); *A61Q 7/00* (2013.01); *A61Q 19/008* (2013.01); *C07C 15/04* (2013.01); *C07C 231/02* (2013.01); *C07C 233/57* (2013.01); *C07C 233/58* (2013.01); *C07C 233/59* (2013.01); *C07C 233/60* (2013.01); *C07C 233/63* (2013.01); *C07C 265/12* (2013.01); *C07D 263/56* (2013.01); *A61K 31/4184* (2013.01); *C07C 2603/74* (2017.05)

(58) Field of Classification Search
CPC ........................... C07C 233/59; A61K 31/165
USPC ........... 514/613; 564/123; 546/134; 548/152
See application file for complete search history.

(56) References Cited

U.S. PATENT DOCUMENTS

| | | | | |
|---|---|---|---|---|
| 3,944,675 | A | * | 3/1976 | Symchowicz ....... C07D 317/58 514/623 |
| 6,201,024 | B1 | | 3/2001 | Baxter et al. |
| 6,242,470 | B1 | | 6/2001 | Baxter et al. |
| 6,348,625 | B1 | | 2/2002 | Anderson |
| 7,220,532 | B2 | * | 5/2007 | Takata .................. G03F 7/0045 430/270.1 |
| 2008/0027049 | A1 | | 1/2008 | Welmaker et al. |
| 2011/0086405 | A1 | | 4/2011 | Tomikawa et al. |

FOREIGN PATENT DOCUMENTS

| | | |
|---|---|---|
| DE | 2254566 A1 | 5/1973 |
| GB | 1412617 A | 11/1975 |
| JP | S4857939 A | 8/1973 |
| JP | S50100001 A | 8/1975 |
| JP | 2003500480 A | 1/2003 |

(Continued)

OTHER PUBLICATIONS

PubChem CID 2838902, 2005.*
PubChem CID 2380238, 2005.*
PubChem CID 584807 (Year: 2005).*
PubChem CID 5151025 (Year: 2005).*
PubChem CID 2912275 (Year: 2005).*
Pub Chem CID 84378085, Oct. 21, 2014 (Year: 2014).*
Pub Chem CID 9839777 (Year: 2006).*
PubChem CID 9861362 (Year: 2006).*

(Continued)

*Primary Examiner* — Shengjun Wang
(74) *Attorney, Agent, or Firm* — Cantor Colburn LLP

(57) ABSTRACT

Disclosed is a novel adamantine derivative compound, an isomer thereof, pharmaceutically acceptable salt thereof, prodrug thereof, hydrate thereof or a solvate thereof. Also disclosed is a method for preparing a novel adamantine derivative compound, an isomer thereof, pharmaceutically acceptable salt thereof, prodrug thereof, hydrate thereof or a solvate thereof. The novel adamantane derivative compound or the like has an excellent anti-androgenic effect.

12 Claims, No Drawings

(56) References Cited

FOREIGN PATENT DOCUMENTS

| JP | 2006522744 | A | 10/2006 |
|---|---|---|---|
| JP | 2008536818 | A | 9/2008 |
| JP | 2011524391 | A | 9/2011 |
| JP | 2013505942 | A | 2/2013 |
| KR | 100858224 | B1 | 9/2008 |
| KR | 1020110064989 | A | 6/2011 |
| KR | 1020130037405 | A | 4/2013 |
| TW | 200408907 | | 9/2010 |
| WO | 0073283 | A1 | 12/2000 |
| WO | 2004089415 | A2 | 10/2004 |
| WO | 2006100502 | A1 | 9/2006 |
| WO | 2009035997 | A2 | 3/2009 |
| WO | 2010003533 | A2 | 1/2010 |
| WO | 2011038152 | A2 | 3/2011 |

OTHER PUBLICATIONS

International Search Report with English Translation for International Application No. PCT/KR2015/008816 dated Nov. 25, 2015.
Rho, et al., Studies on depigmenting activities of dihydroxyl benzamide derivatives containing adamantane moiety, Bioorganic & Medicinal Chemistry Letters, vol. 19 (2009) pp. 1532-1533.
Alfred Kreutzberger et al., "Potentiell Virushemmende N-[Adamantyl-(1)]-Carbonsäureamide", Tetrahedron Letters, No. 52, 1970, pp. 4523-4526 (see p. 4524, compounds IVb, IVc, IVd, IVe cited as relevant by Extended European Search Report).
Office Action dated Dec. 3, 2018 for CN Application No. 201580055458. X, with English Translation.
Extended European Search Report dated Apr. 5, 2018, for EP application No. 15835660.0.
Adam R. Renslo, et al., "Synthesis and Assembly of Self-Complementary Cavitands", J. Am. Chem. Soc. 2000, 122, 4573-4582.
Carolina Benedi, et al., "Synthesis of 2-substituted-benzothiazoles by palladium-catalyzed intramolecular cyclization of o-bromophenylthioureas and o bromophenylthioamides", Tetrahedron Letters 44 (2003) 6073-6077.
E. A. Dikusar. et al., "Synthesis of New 1-Adamantanecarboxylic Acid Derivatives", Russian Journal of Organic Chemistry, vol. 40, No. 3, 2004, pp. 346-352.
Elvira Shokova, et al., "Adamantylation and Adamantylalkylation of Amides, Nitriles and Ureas in Trifluoroacetic Acid", Synthesis, 1997, vol. 9, pp. 1034-1040.

Habib Firouzabadi, et al., "Dodecatungstophosphoric acid (H3PW12O40) as a highly efficient catalyst for the amidation of alcohols and protectedalcohols with nitriles in water: A modified Ritter reaction", Catalysis Communications 9 (2008) 529-531.
Heung Soo Baek, et al., "The Inhibitory Effect of New Hydroxamic Acid Derivatives on Melanogenesis", Bull. Korean Chem. Soc. 2008, vol. 29, No. 1, pp. 43-46.
Hyunwoo Kim, et al., "Iridium-Catalyzed C—H Amination with Anilines at Room Temperature: Compatibility of Iridacycles with External Oxidants", J. Am. Chem. Soc. 2014, 136, 5904-5907.
Japanese Office Action with English Translation dated Mar. 26, 2019, Application No. 2017511650, 13 pages.
Padraick J. Dornbush, et al., "Preliminary studies of 3,4-dichloroaniline amides as antiparasitic agents: Structure-activity analysis of a compound library in vitro against Trichomonas vaginalis", Bioorganic & Medicinal Chemistry Letters 20 (2010) 5299-5301.
Xu Hui, et al., "Synthesis and antiprotozoal activity of some new synthetic substituted quinoxalines", Bioorganic & Medicinal Chemistry Letters 16 (2006) 815-820.
Xiangdong Su, et al., "Discovery of novel inhibitors of human 11beta-hydroxysteroid dehydrogenase type 1", Molecular and Cellular Endocrinology 301 (2009) 169-173.
Rajesh Kumar Rapolu, et al., "Silica sulfuric acid: a reusable solid catalyst for the synthesis of N-substituted amides via the Ritter reaction", RSC Advances, 2013, 3, 5332-5337.
Sarah A. Stanley, et al., "Identification of Novel Inhibitors of M. tuberculosis Growth Using Whole Cell Based High-Throughput Screening", ACS Chem. Biol. 2012, 7, 1377-1384.
Wagner G, Briel D., "Covalent binding of 1-aminoadamantan derivatives to protein antigens using the isothiocyanate and the imidic acid ester procedures. Part 27:Immunosuppressive agent-antigent conjugates", Pharmazie, 1981, 4 pp. (Machine English translation of abstract only).
Database Registry, Posted Aug. 4, 2003, p. 1, retrieved from the Internet Jun. 11, 2019, <URL:https://stnweb-japan.cas.org/>.
Database Registry, Posted Jun. 23, 2003, p. 1, retrieved from the Internet Jun. 11, 2019, <URL:https://stnweb-japan.cas.org/>.
Database Registry, Posted Oct. 16, 2002, p. 1, retrieved from the Internet Jun. 11, 2019, <URL:https://stnweb-japan.cas.org/>.
Japanese Office Action—Japanese Patent Application No. 2017-511650 dated Jun. 11, 2019, citing references listed within instant IDS.

* cited by examiner

ADAMANTANE DERIVATIVE COMPOUND

TECHNICAL FIELD

The present disclosure relates to a novel adamantane derivative compound and use thereof for inhibiting androgen.

BACKGROUND ART

As males and females suffering from hereditary or environmental alopecia increase in the modern society that values beauty, various studies have been conducted actively all over the world to develop a method for treating alopecia and stimulating hair growth.

Human hairs exist in a number of about 100-150 thousands and each hair repeats growth and atrophy through a different cycle. Hairs repeat a three-step cycle including the anagen in which hair growth occurs, the catagen in which hairs, after the completion of the anagen, undergo slow-down in metabolic process while maintaining its shape, and the telogen in which hair papillae shrink and follicles gradually shrink, resulting in push-up of hair roots and reduction of follicles. Such a cycle and life of hairs may be varied with various conditions, including nourishment, medical history, heredity, constitution, hormone secretion and aging. In the case of a human, the whole hairs are not present at the same follicle cycle and several thousands of hairs exist in each of the three phases.

Meanwhile, most hairs are present in the anagen. Particularly, in the case of a healthy young adult, hairs are present in the anagen and telogen at a ratio of about 9:1. In the case of a patient suffering from alopecia, the ratio decreases to about 2:1.

Male pattern alopecia, the most common type of alopecia, is caused by activation of hereditary sensitivity to circulating androgen hormone. This may occur both in males (50%) and females (30%), and mainly in the white race. As aging proceeds, in a part of alopecia cases, the width and length between one hair and another hair are gradually changed prematurely, and thus terminals hairs are gradually converted into short and sparse colorless soft hairs. In the case of a man, most alopecia occurs at the crown of the head. In the case of a woman, hairs become sparse in the whole part of scalp.

Among the existing anti-alopecia treating agents, minoxidil, an external application agent the use of which is approved by FDA in USA based on its effect, is known to be effective for inducing hairs in the telogen to hairs in the anagen and maintaining the induced anagen cycle of hairs continuously, in addition to a vasodilatation function as a potassium channel opener. However, many people regard hair growth caused by minoxidil as insufficient in cosmetic effects. Therefore, three is a need for developing a material inducing hair growth at a higher rate while satisfying a cosmetic effect sufficiently.

REFERENCES

Patent Documents

Korean Laid-Open Patent No. 10-2011-0064989 (2011 Jun. 15)
Korean Patent Publication No. 10-0858224 (2008 Sep. 4)
Korean Laid-Open Patent No. 10-2013-0037405 (2013 Apr. 16)

DISCLOSURE

Technical Problem

A technical problem to be solved by the present disclosure is to provide a novel adamantane derivative compound.

Another technical problem to be solved by the present disclosure is to provide a compositing having an anti-androgenic effect.

Still another technical problem to be solved by the present disclosure is to provide a composition having an effect of stimulating hair growth.

Still another technical problem to be solved by the present disclosure is to provide a composition having an anti-sebum effect.

Yet another technical problem to be solved by the present disclosure is to provide a method for preparing a novel adamantane derivative compound.

Technical Solution

In one general aspect, there is provided a compound represented by the following Chemical Formula 1, an isomer thereof, pharmaceutically acceptable salt thereof, prodrug thereof, hydrate thereof or a solvate thereof:

[Chemical Formula 1]

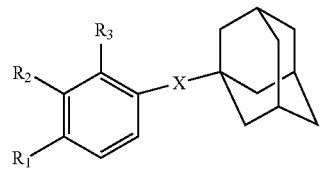

wherein X is —NHCO— or —CONH—; each of $R_1$ and $R_2$ is independently substituted, $R_1$ is selected from the group consisting of hydrogen, halogen, $NO_2$, $C_1$-$C_6$ alkoxy, CN, $CO_2Me$, $CO_2H$ and $NH_2$, and $R_2$ is selected from the group consisting of hydrogen, $C_1$-$C_6$ alkoxy, $C_1$-$C_6$ alkyl and halogen; or $R_1$ and $R_2$ are linked to each other to form a cyclic carbon chain optionally containing a hetero atom, wherein the cyclic carbon chain is selected from the group consisting of $C_2$-$C_{18}$ cycloalkyl, $C_4$-$C_{18}$ aryl, $C_2$-$C_{18}$ heterocycloalkyl in which at least one carbon is substituted with at least one hetero atom selected from nitrogen, oxygen and sulfur, and $C_4$-$C_{18}$ heteroaryl in which at least one carbon is substituted with at least one hetero atom selected from nitrogen, oxygen and sulfur; and $R_3$ is selected from the group consisting of hydrogen, $C_1$-$C_6$ alkoxy and halogen.

According to an embodiment, $R_2$ may be selected from the group consisting of hydrogen, $C_1$-$C_3$ alkoxy, $C_1$-$C_3$ alkyl and halogen.

According to another embodiment, $R_1$ and $R_2$ may be linked to each other to form a carbon chain or hetero atom-containing chain selected from the group consisting of 1,3-dioxole, 1,3-thiazole, 1,3-oxazole, pyridyl and cyclobutyl.

According to still another embodiment, the halogen may be chloride.

According to still another embodiment, $R_1$ may be $NO_2$ or CN, $R_2$ may be hydrogen, methyl, methoxy or chloride, and $R_3$ may be hydrogen, methoxy or chloride.

According to still another embodiment, when $R_3$ is hydrogen and $R_2$ is halogen, $R_2$ may be chloride.

According to yet another embodiment, the compound may be one selected from the group consisting of adamantan-1-carboxylic acid-(3-methyl-4-nitrophenyl)amide; adamantan-1-carboxylic acid-(3-methoxy-4-nitrophenyl)amide; adamantan-1-carboxylic acid-(3-chloro-4-nitrophenyl)amide; adamantan-1-carboxylic acid-(2-chloro-4-nitrophenyl)amide; adamantan-1-carboxylic acid-(4-cyano-3-methoxy-phenyl)amide; adamantan-1-carboxylic acid-(4-cyano-2-chloro-phenyl)amide; N-adamantan-1-yl-N-(4-nitro-3-methyl-phenyl)-acetamide; N-adamantan-1-yl-N-(4-nitro-3-methoxy-phenyl)-acetamide; N-adamantan-1-yl-N-(4-nitro-3-chloro-phenyl)-acetamide; N-adamantan-1-yl-N-(4-nitro-2-chloro-phenyl)-acetamide; adamantan-1-carboxylic acid benzo[1,3]dioxol-5-ylamide; adamantan-1-carboxylic acid benzothiazol-6-ylamide; adamantan-1-carboxylic acid (3-methoxyphenyl)amide; adamantan-1-carboxylic acid (4-nitrophenyl)amide; adamantan-1-carboxylic acid phenylamide; adamantan-1-carboxylic acid (3,4-dimethoxyphenyl)amide; adamantan-1-carboxylic acid (4-fluoro-3-methoxyphenyl)amide; adamantan-1-carboxylic acid benzoxazol-6-ylamide; adamantan-1-carboxylic acid (4-bromo-3-methoxyphenyl)amide; adamantan-1-carboxylic acid quinolin-6-ylamide; 4-[(adamantan-1-carbonyl)-amino]2-methoxy-benzoic acid methylester; adamantan-1-carboxylic acid (4-methoxyphenyl)amide; adamantan-1-carboxylic acid (3-nitrophenyl)amide; adamantan-1-carboxylic acid (5,6,7,8-tetrahydronaphthalen-2-yl)amide; adamantan-1-carboxylic acid (2-methoxy-4-nitrophenyl)amide; and 4-[(adamantan-1-carbonyl)-amino]-2-methoxy-benzoic acid, an isomer thereof, pharmaceutically acceptable salt thereof, prodrug thereof, hydrate thereof, or a solvate thereof.

In another general aspect, there is provided a composition including a compound represented by Chemical Formula 1, an isomer thereof, pharmaceutically acceptable salt thereof, prodrug thereof, hydrate thereof, or a solvate thereof.

According to an embodiment, the composition may be a skin application composition.

According to another embodiment, the composition may be an anti-androgenic composition.

According to still another embodiment, the composition may be a composition for stimulating hair growth.

According to still another embodiment, the composition may be an anti-sebum composition.

According to yet another embodiment, the composition may include the compound represented by Chemical Formula 1, an isomer thereof, pharmaceutically acceptable salt thereof, prodrug thereof, hydrate thereof, or a solvate thereof, in an amount of 0.01 wt %-20 wt % based on the total weight of the composition.

In still another general aspect, there is provided a method for preparing a compound represented by Chemical Formula 1, an isomer thereof, pharmaceutically acceptable salt thereof, prodrug thereof, hydrate thereof, or a solvate thereof, the method including reacting a compound represented by the following Chemical Formula 2 or 3 with a benzoic acid salt derivative or phenylamine derivative in the presence of a base:

[Chemical Formula 2]

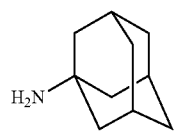

[Chemical Formula 3]

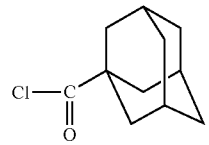

Advantageous Effects

According to an aspect of the present disclosure, the novel adamantane derivative compound, an isomer thereof, pharmaceutically acceptable salt thereof, prodrug thereof, hydrate thereof, or a solvate thereof has an effect of inhibiting androgen.

The novel adamantane derivative compound, an isomer thereof, pharmaceutically acceptable salt thereof, prodrug thereof, hydrate thereof, or a solvate thereof has an excellent anti-alopecia effect.

The novel adamantane derivative compound, an isomer thereof, pharmaceutically acceptable salt thereof, prodrug thereof, hydrate thereof, or a solvate thereof has an effect of stimulating hair growth.

The novel adamantane derivative compound, an isomer thereof, pharmaceutically acceptable salt thereof, prodrug thereof, hydrate thereof, or a solvate thereof has an anti-sebum effect.

According to another aspect of the present disclosure, it is possible to provide a novel adamantane derivative compound, an isomer thereof, pharmaceutically acceptable salt thereof, prodrug thereof, hydrate thereof, or a solvate thereof having the above-mentioned effects.

BEST MODE

The inventors of the present disclosure have conducted intensive studies to find a material having an excellent anti-alopecia effect and effect of stimulating hair growth while showing no side effects. As a result, we have found that adamantane derivatives have an excellent anti-androgenic effect and provide an excellent anti-alopecia effect and effect of stimulating hair growth. The present disclosure is based on this finding.

Definition

As used herein, the term 'skin' means tissues covering the body surface of an animal, and is used in its broadest concept including not only tissues covering the surface of a face or body but also the scalp and hair. In addition, the term 'hair' covers hair in the body and hair in the head. The term 'hair' also includes not only human hair but also animal hair. As used herein, 'stimulating hair growth' means not only stimulating generation of new hair but also allowing the existing hair to grow in a healthy state, and thus is used in a concept that covers preventing alopecia and stimulating hair growth.

As used herein, the term 'alkyl' means a monovalent saturated aliphatic hydrocarbon chain. The hydrocarbon chain may be linear or branched. According to an embodiment, 'alkyl' may have 1-6 carbon atoms ('$C_1$-$C_6$ alkyl'). According to another embodiment, 'alkyl' may have 1-5 carbon atoms ('$C_1$-$C_5$ alkyl'), 1-4 carbon atoms ('$C_1$-$C_4$ alkyl'), or 1-3 carbon atoms ('$C_1$-$C_3$ alkyl'). Particularly, 'alkyl' may include methyl, ethyl, n-propyl, isopropyl, n-butyl, iso-butyl, tert-butyl or t-amyl, but is not limited thereto.

As used herein, the term 'alkoxy' means —OR group, wherein R means the alkyl group as defined above. Particularly, 'alkoxy' may include methoxy, ethoxy, n-propoxy, isopropoxy, n-butoxy, tert-butoxy, sec-butoxy, n-pentoxy or 1,2-dimethylbutoxy, or the like, but is not limited thereto.

As used herein, the term 'halogen' includes fluoro, chloro, bromo or iodo. According to an embodiment, halogen may be chloro (chloride).

As used herein, the term 'isomers' particularly includes not only optical isomers (such as essentially pure enantiomers, essentially pure diastereomers or a mixture thereof) but also conformation isomers (i.e., isomers having a different angle in at least one chemical bond), position isomers (particularly, tautomers) or geometric isomers (e.g. cis-trans isomers).

As used herein, 'essentially pure', when used with reference to enantiomers or diastereomers, for example, means that a specific compound that may be exemplified by an enantiomer or diastereomer is present in an amount of about 90% or more, preferably about 95% or more, more preferably about 97% or more, or about 98% or more, even more preferably about 99% or more, even much more preferably about 99.5% (w/w).

As used herein, 'pharmaceutically acceptable' means that use of a general medicinal dosage avoids a significant toxic effect and thus can be accepted or is accepted as appropriate in application to animals, particularly to humans by the government or the corresponding regulation organization, or is listed in the pharmacopeia or regarded as general pharmacopeia.

As used herein, 'pharmaceutically acceptable salt' means a salt according to an aspect of the present disclosure that is pharmaceutically acceptable and has desired pharmacological activity of the parent compound. The salt may include: (1) acid addition salt formed with an inorganic acid, such as hydrochloric acid, hydrobromic acid, sulfuric acid, nitric acid or phosphoric acid, or with an organic acid, such as acetic acid, propionic acid, hexanoic acid, cyclopentanepropionic acid, glycolic acid, pyrubic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tert-butylacetic acid, laurylsulfuric acid, gluconic acid, glutamic acid, hydroxynaphthoic acid, salicylic acid, stearic acid or muconic acid; or (2) a salt formed upon the substitution of an acidic proton present in the parent compound.

As used herein, the term 'prodrug' means a drug having controlled physical and chemical properties by modifying a compound chemically, and does not show physiological activity in itself but is converted into the original compound in vivo after administration by the action of chemicals or enzymes to realize pharmaceutical effects.

As used herein, the term 'hydrate' means a compound to which water is bound and is used in its broadest concept including an inclusion compound having no chemical binding force between water and a compound.

As used herein, the term 'solvate' means a high-degree compound generated between a molecule or ion of solute and a molecule or ion of solvent.

In one aspect, there is provided a compound represented by the following Chemical Formula 1, an isomer thereof, pharmaceutically acceptable salt thereof, prodrug thereof, hydrate thereof or a solvate thereof:

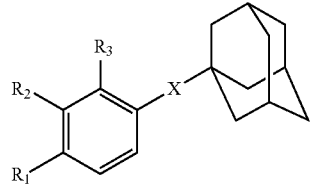

[Chemical Formula 1]

wherein X is —NHCO— or —CONH—; each of $R_1$ and $R_2$ is independently substituted, $R_1$ is selected from the group consisting of hydrogen, halogen, $NO_2$, $C_1$-$C_6$ alkoxy, CN, $CO_2Me$, $CO_2H$ and $NH_2$, and $R_2$ is selected from the group consisting of hydrogen, $C_1$-$C_6$ alkoxy, $C_1$-$C_6$ alkyl and halogen; or $R_1$ and $R_2$ are linked to each other to form a cyclic carbon chain optionally containing a hetero atom, wherein the cyclic carbon chain is selected from the group consisting of $C_2$-$C_{18}$ cycloalkyl, $C_4$-$C_{18}$ aryl, $C_2$-$C_{18}$ heterocycloalkyl in which at least one carbon is substituted with at least one hetero atom selected from nitrogen, oxygen and sulfur, and $C_4$-$C_{18}$ heteroaryl in which at least one carbon is substituted with at least one hetero atom selected from nitrogen, oxygen and sulfur; and $R_3$ is selected from the group consisting of hydrogen, $C_1$-$C_6$ alkoxy and halogen.

According to an embodiment, $R_2$ may be selected from the group consisting of hydrogen, $C_1$-$C_3$ alkoxy, $C_1$-$C_3$ alkyl and halogen.

According to another embodiment, $R_1$ and $R_2$ may be linked to each other to form a carbon chain or hetero atom-containing chain selected from the group consisting of 1,3-dioxole, 1,3-thiazole, 1,3-oxazole, pyridyl and cyclobutyl.

According to still another embodiment, the halogen may be chloride.

According to still another embodiment, $R_1$ may be $NO_2$ or CN, $R_2$ may be hydrogen, methyl, methoxy or chloride, and $R_3$ may be hydrogen, methoxy or chloride.

According to still another embodiment, when $R_3$ is hydrogen and $R_2$ is halogen, $R_2$ may be chloride.

According to yet another embodiment, the compound may be one selected from the group consisting of adamantan-1-carboxylic acid-(3-methyl-4-nitrophenyl)amide; adamantan-1-carboxylic acid-(3-methoxy-4-nitrophenyl)amide; adamantan-1-carboxylic acid-(3-chloro-4-nitrophenyl)amide; adamantan-1-carboxylic acid-(2-chloro-4-nitrophenyl)amide; adamantan-1-carboxylic acid-(4-cyano-3-methoxy-phenyl)amide; adamantan-1-carboxylic acid-(4-cyano-2-chloro-phenyl)amide; N-adamantan-1-yl-N-(4-nitro-3-methyl-phenyl)-acetamide; N-adamantan-1-yl-N-(4-nitro-3-methoxy-phenyl)-acetamide; N-adamantan-1-yl-N-(4-nitro-3-chloro-phenyl)-acetamide; N-adamantan-1-yl-N-(4-nitro-2-chloro-phenyl)-acetamide; adamantan-1-carboxylic acid benzo[1,3]dioxol-5-ylamide; adamantan-1-carboxylic acid benzothiazol-6-ylamide; adamantan-1-carboxylic acid (3-methoxyphenyl)amide; adamantan-1-carboxylic acid (4-nitrophenyl)amide; adamantan-1-carboxylic acid phenylamide; adamantan-1-carboxylic acid (3,4-dimethoxyphenyl)amide; adamantan-1-carboxylic acid (4-fluoro-3-methoxyphenyl)amide; adamant-1-carboxylic acid benzoxazol-6-ylamide; adamantan-1-carboxylic acid (4-bromo-3-methoxyphenyl)amide; adamantan-1-carboxylic acid quinolin-6-ylamide; 4-[(adamantan-1-carbonyl)- amino]2-methoxy-benzoic acid methylester; adamantan-1-carboxylic acid (4-methoxyphenyl)amide; adamantan-1-carboxylic acid (3-nitrophenyl)amide; adamantan-1-carboxylic acid (5,6,7,8-tetrahydronaphthalen-2-yl)amide; adamantan-1-carboxylic acid)2-methoxy-4-nitrophenyl)amide; and 4-[(adamantan-1-carbonyl)-amino]-2-methoxy-benzoic acid, an isomer thereof, pharmaceutically acceptable salt thereof, prodrug thereof, hydrate thereof, or a solvate thereof.

In another aspect, there is provided a composition including a compound represented by Chemical Formula 1, an isomer thereof, pharmaceutically acceptable salt thereof, prodrug thereof, hydrate thereof, or a solvate thereof.

According to an embodiment, the composition may be a skin application composition.

According to another embodiment, the composition may be an anti-androgenic composition. The above-mentioned compound, an isomer thereof, pharmaceutically acceptable salt thereof, prodrug thereof, hydrate thereof, or a solvate thereof shows an excellent anti-androgenic effect, which can be determined by the competitive binding of the compound with DHT (dihydrotestosterone) to an androgen receptor.

In still another aspect, there is provided a method for enhancing an anti-androgenic effect in a subject, the method including administering an effective amount of a compound represented by the above Chemical Formula 1, an isomer thereof, pharmaceutically acceptable salt thereof, prodrug thereof, hydrate thereof, or a solvate thereof to a subject in need thereof.

In still another aspect, there is provided use of a compound represented by the above Chemical Formula 1, an isomer thereof, pharmaceutically acceptable salt thereof, prodrug thereof, hydrate thereof, or a solvate thereof in preparing a composition for enhancing an anti-androgenic effect.

In still another aspect, there is provided a compound represented by the above Chemical Formula 1, an isomer thereof, pharmaceutically acceptable salt thereof, prodrug thereof, hydrate thereof, or a solvate thereof for use in enhancing an anti-androgenic effect.

According to an embodiment, the composition is a composition for stimulating hair growth. The composition including the compound, an isomer thereof, pharmaceutically acceptable salt thereof, prodrug thereof, hydrate thereof, or a solvate thereof as an active ingredient inhibits androgen, stimulates proliferation of hair papilla cells of hair follicle cells and hair growth and controls excessive secretion of sebum, and thus has an excellent anti-alopecia effect, pilatory effect and hair growth-stimulating effect. Herein, alopecia may include male pattern alopecia.

In still another aspect, there is provided a method for enhancing an anti-alopecia effect, pilatory effect and hair growth-stimulating effect in a subject, the method including administering an effective amount of a compound represented by the above Chemical Formula 1, an isomer thereof, pharmaceutically acceptable salt thereof, prodrug thereof, hydrate thereof, or a solvate thereof to a subject in need thereof.

In still another aspect, there is provided use of a compound represented by the above Chemical Formula 1, an isomer thereof, pharmaceutically acceptable salt thereof, prodrug thereof, hydrate thereof, or a solvate thereof in preparing a composition for enhancing an anti-alopecia effect, pilatory effect and hair growth-stimulating effect.

In still another aspect, there is provided a compound represented by the above Chemical Formula 1, an isomer thereof, pharmaceutically acceptable salt thereof, prodrug thereof, hydrate thereof, or a solvate thereof for use in enhancing an anti-alopecia effect, pilatory effect and hair growth-stimulating effect.

According to an embodiment, the composition may be an anti-sebum composition. When sebum is secreted excessively from the sebaceous glands or inflammation is generated, skin troubles, such as follicle extension or acne, occur. The composition including the compound, an isomer thereof, pharmaceutically acceptable salt thereof, prodrug thereof, hydrate thereof, or a solvate thereof as an active ingredient inhibits androgen and controls secretion of sebum, and improves follicle extension, acne or skin troubles.

In still another aspect, there is provided a method for enhancing an anti-sebum effect in a subject, the method including administering an effective amount of a compound represented by the above Chemical Formula 1, an isomer thereof, pharmaceutically acceptable salt thereof, prodrug thereof, hydrate thereof, or a solvate thereof to a subject in need thereof.

In still another aspect, there is provided use of a compound represented by the above Chemical Formula 1, an isomer thereof, pharmaceutically acceptable salt thereof, prodrug thereof, hydrate thereof, or a solvate thereof in preparing a composition for enhancing an anti-sebum effect.

In still another aspect, there is provided a compound represented by the above Chemical Formula 1, an isomer thereof, pharmaceutically acceptable salt thereof, prodrug thereof, hydrate thereof, or a solvate thereof for use in enhancing an anti-sebum effect.

According to an embodiment, the composition may include a compound represented by the above Chemical Formula 1, an isomer thereof, pharmaceutically acceptable salt thereof, prodrug thereof, hydrate thereof, or a solvate thereof in an amount of 0.01 wt %-20 wt % based on the total weight of the composition.

Particularly, the composition may include a compound represented by the above Chemical Formula 1, an isomer thereof, pharmaceutically acceptable salt thereof, prodrug thereof, hydrate thereof, or a solvate thereof in an amount of at least 0.01 wt %, at least 0.1 wt %, at least 1 wt %, at least 2 wt %, at least 3 wt %, at least 4 wt % or at least 5 wt % based on the total weight of the composition.

In addition, the composition may include a compound represented by the above Chemical Formula 1, an isomer thereof, pharmaceutically acceptable salt thereof, prodrug thereof, hydrate thereof, or a solvate thereof in an amount of at most 20 wt %, at most 18 wt %, at most 16 wt %, at most 14 wt %, at most 12 wt %, at most 10 wt %, at most 8 wt %, at most 6 wt % or at most 5 wt % based on the total weight of the composition.

More particularly, the composition may include a compound represented by the above Chemical Formula 1, an isomer thereof, pharmaceutically acceptable salt thereof, prodrug thereof, hydrate thereof, or a solvate thereof in an amount of 0.5 wt %-5 wt % based on the total weight of the composition.

Within the above-defined range, it is possible to provide a desired effect of the present disclosure and to satisfy both the stability and safety of the composition. In addition, the above-defined range is suitable when viewed from cost efficiency. Particularly, when using the adamantane derivative compound, an isomer thereof, pharmaceutically acceptable salt thereof, prodrug thereof, hydrate thereof, or a solvate thereof in an amount less than 0.01 wt %, it is not possible to obtain a sufficient anti-androgenic effect. Use of the adamantane derivative compound, an isomer thereof, pharmaceutically acceptable salt thereof, prodrug thereof, hydrate thereof, or a solvate thereof in an amount more than 20 wt % is not preferable in terms of cost efficiency.

In still another aspect, there is provided a skin application composition including the adamantane derivative compound, an isomer thereof, pharmaceutically acceptable salt thereof, prodrug thereof, hydrate thereof, or a solvate thereof. In still another aspect, there is provided a cosmetic composition including the adamantane derivative compound, an isomer thereof, pharmaceutically acceptable salt thereof, prodrug thereof, hydrate thereof, or a solvate thereof. In still another aspect, the cosmetic composition may provide an effect of preventing or treating alopecia, hair growth-stimulating effect, hair health-enhancing effect and an anti-sebum effect.

The cosmetic composition may be provided in any form suitable for local application, such as solution, gel, solid, anhydrous slurry product, oil-in-water emulsion, water-in-oil emulsion, multi-emulsion, suspension, microemulsion, microcapsules, microgranules or ionic (liposome) or non-ionic vesicular dispersion. Such a composition may be obtained by the method generally known in the art.

The cosmetic composition may further include other conventional ingredients depending on its form, and such conventional ingredients are known to those skilled in the art. In addition, the cosmetic composition may further include other ingredients known to stimulate hair growth and prevent alopecia, in addition to the adamantane derivative compound, an isomer thereof, pharmaceutically acceptable salt thereof, prodrug thereof, hydrate thereof, or a solvate thereof. The type and amount of such ingredients known to stimulate hair growth and prevent alopecia will be apparent to those skilled in the art.

There is no particular limitation in the form of the cosmetic composition and any suitable form may be selected depending on particular use. For example, the cosmetic composition may be provided in at least one form selected from the group consisting of hair shampoo, hair conditioner, hair treatment, hair essence, hair serum, hair lotion, hair cream, scalp hair tonic, scale essence, scalp cream, hair gel, hair spray and hair pack, but is not limited thereto. The hair cosmetic composition according to an aspect of the present disclosure may be one to be applied to hair or scalp.

In still another aspect, there is provided a pharmaceutical composition including the adamantane derivative compound, an isomer thereof, pharmaceutically acceptable salt thereof, prodrug thereof, hydrate thereof, or a solvate thereof. In still another aspect, the pharmaceutical composition is effective for preventing or treating alopecia, enhancing hair health, and inhibiting secretion of sebum.

The pharmaceutical composition according to an aspect of the present disclosure may be administered via an oral, parenteral, rectal, local, transdermal, intravenous, intramuscular, intraperitoneal or subcutaneous route, or the like. Formulations for oral administration may include tablets, pills, soft and hard capsules, granules, powder, microparticles, liquid, emulsion or pellets, but is not limited thereto. Formulations for parenteral administration may include a solution, suspension, milky liquid, gel, injection formulation, drops, suppository, patch or a spray agent, but is not limited thereto. Such formulations may be obtained by the conventional method with ease, and optionally use surfactants, excipients, hydrating agents, emulsification accelerating agents, suspending agents, salts or buffers for adjusting osmotic pressure, colorants, fragrance, stabilizing agents, antiseptics, preservatives or other conventional supplements.

In the pharmaceutical composition according to an aspect of the present disclosure, the dosage of active ingredient depends on the age, sex and body weight of a subject to be administered, condition of disease and severity thereof, administration route or the judge of a prescriber. The dosage may be determined by those skilled in the art on the basis of the above factors. For example, the daily dosage may be 0.1 µg/kg/day to 5000 mg/kg/day, particularly 50 mg/kg/day to 500 mg/kg/day, but is not limited thereto.

In yet another aspect, there is provided a method for preparing a compound represented by Chemical Formula 1, an isomer thereof, pharmaceutically acceptable salt thereof, prodrug thereof, hydrate thereof, or a solvate thereof, the method including reacting a compound represented by the following Chemical Formula 2 or 3 with a benzoic acid salt derivative or phenylamine derivative in the presence of a base:

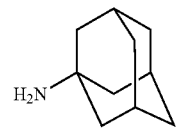

[Chemical Formula 2]

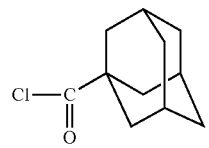

[Chemical Formula 3]

According to an embodiment, the benzoic acid derivative or phenylamine derivative includes a benzoic acid salt or phenyl amine in which at least one of $R_1$, $R_2$ and $R_3$ is substituted, particularly in at least one of 4-position, 3-position and 2-position, wherein $R_1$ is selected from the group consisting of $NO_2$, CN and $NH_2$, $R_2$ is selected from the group consisting of $C_1$-$C_6$ alkoxy, $C_1$-$C_6$ alkyl and halogen, and $R_3$ is hydrogen or halogen.

According to another embodiment, the method according to an aspect of the present disclosure may be carried out by any one process selected from the group consisting of an acid halide process, active ester process and acid anhydride process. According to another embodiment, the method may be carried out by using an acid halide process, particularly by using a base having an oleophilic group. In this case, when the equivalent ratio of the reactant, acid halide, to the base having an oleophilic group is less than 1.1, the target product is obtained in a small amount. Thus, it is preferred that the ratio of the acid halide to the base is 1.1-1.3.

According to still another embodiment, the base includes pyridine or trimethylamine. It is preferred to use trimethylamine. According to still another embodiment, at least one reaction solvent selected from the group consisting of dichloromethane, acetone, N,N-dimethyl formamide, acetonitrile and tetrahydrofuran may be used. It is preferred to use dichloromethane. According to yet another embodiment, it is suitable that the reaction temperature is 10-70° C., preferably 10-40° C.

The method for preparing a compound represented by the above Chemical Formula 1 may be depicted by the following Reaction Scheme 1:

[Reaction Scheme 1]

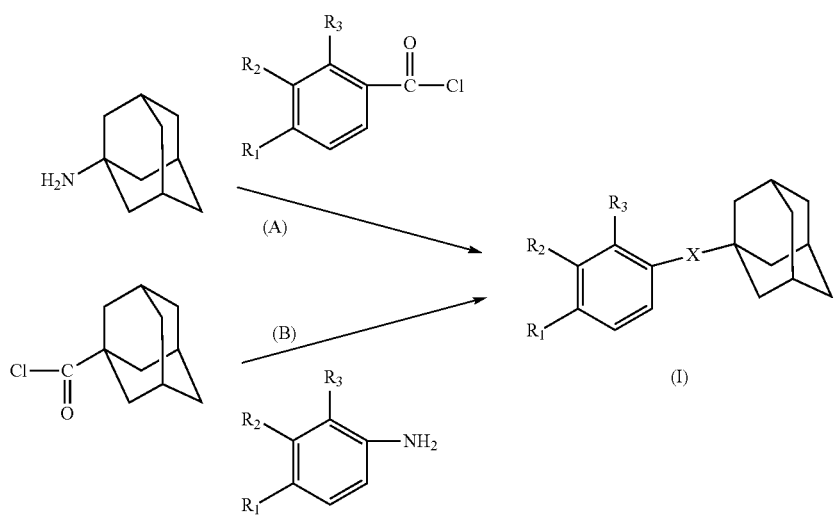

According to step (A) of Reaction Scheme 1, X is —NHCO—. According to step (B), X is —CONH—. R₁, R₂ and R₃ are the same as defined above.

Hereinafter, the constitution and effect of the present disclosure will be explained in detail with reference to examples and test examples. The following examples and test examples are for illustrative purposes only and not intended to limit the scope of the present disclosure.

[Example 1] Preparation of Adamantan-1-carboxylic acid-(3-methyl-4-nitrophenyl)-amide

[Chemical Formula 4]

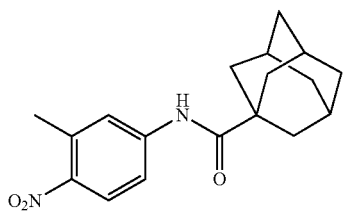

First, 3-methyl-4-nitroaniline (100 mg, 0.65 mmol, 1.1 eq) is dissolved into pyridine (1 ml). Next, adamantane carboxyl chloride (118 mg, 0.59 mmol, 1.0 eq) is added gradually dropwise thereto at 0° C. The reaction mixture is agitated at room temperature for 3 hours. The reaction mixture is introduced to and diluted with ethyl acetate. Then, the reaction mixture is washed with 1N aqueous hydrochloric acid twice. After that, the reaction mixture is washed with saline, dried over dry manganese (100 mg), filtered, concentrated and separated by column chromatography to obtain 164 mg of the target product (yield 84%). The NMR results of the product are shown below. It can be seen from the NMR results that the product is adamantan-1-carboxylic acid-(3-methyl-4-nitrophenyl)-amide.

¹H NMR (300 MHz, CDCl₃, δ): 8.03 (d, 1H, J=9.0 Hz), 7.62 (s, 1H), 7.51-7.48 (m, 2H), 2.62 (s, 3H), 2.11 (s, 3H), 1.96-1.81 (m, 6H), 1.81-1.71 (m, 6H).

[Example 2] Preparation of Adamantan-1-carboxylic acid-(3-methoxy-4-nitrophenyl)-amide

[Chemical Formula 5]

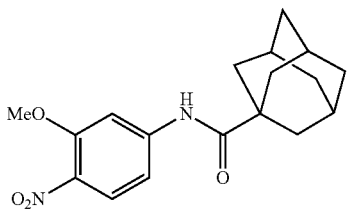

Example 1 is repeated to obtain 71 mg (yield 42%) of the target product as white solid, except that 3-methoxy-4-nitroaniline is used instead of 3-methyl-4-nitroaniline. The NMR results of the product are shown below. It can be seen from the NMR results that the product is adamantan-1-carboxylic acid-(3-methoxy-4-nitrophenyl)-amide.

¹H NMR (300 MHz, CDCl₃, δ): 7.97 (d, 1H, J=2.1 Hz), 7.93 (d, 1H, J=9.0 Hz), 7.51 (s, 1H), 6.76 (dd, 1H, J=2.1 and J=9.0 Hz), 3.98 (s, 3H), 2.13 (s, 3H), 2.04-1.90 (m, 6H), 1.83-1.72 (m, 6H).

[Example 3] Preparation of Adamantan-1-carboxylic acid-(3-chloro-4-nitrophenyl)-amide

[Chemical Formula 6]

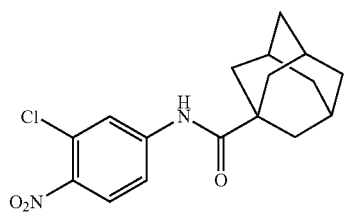

Example 1 is repeated to obtain 94 mg (yield 79%) of the target product as yellow solid, except that 3-chloro-4-nitroaniline is used instead of 3-methyl-4-nitroaniline. The NMR results of the product are shown below. It can be seen from the NMR results that the product is adamantan-1-carboxylic acid-(3-chloro-4-nitrophenyl)-amide.

$^1$H NMR (300 MHz, CDCl$_3$, δ): 7.97-7.92 (m, 2H), 7.54 (dd, 1H, J=2.1 and J=9.0 Hz), 7.52 (s, 1H), 2.12 (s, 3H), 1.96-1.94 (m, 6H), 1.83-1.71 (m, 6H).

[Example 4] Preparation of Adamantan-1-carboxylic acid-(2-chloro-4-nitrophenyl)-amide

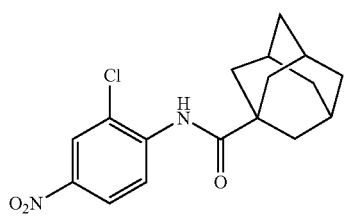

[Chemical Formula 7]

Example 1 is repeated to obtain 101 mg (yield 61%) of the target product as yellow solid, except that 2-chloro-4-nitroaniline is used instead of 3-methyl-4-nitroaniline. The NMR results of the product are shown below. It can be seen from the NMR results that the product is adamantan-1-carboxylic acid-(2-chloro-4-nitrophenyl)-amide.

$^1$H NMR (300 MHz, CDCl$_3$, δ): 8.72 (d, 1H, J=9.0 Hz), 8.29-8.28 (m, 2H), 8.16 (dd, 1H, J=2.7 and J=9.3 Hz), 2.14 (s, 3H), 2.00-1.90 (m, 6H), 1.84-1.73 (m, 6H).

[Example 5] Preparation of Adamantan-1-carboxylic acid-(4-cyano-3-methoxy-phenyl)-amide

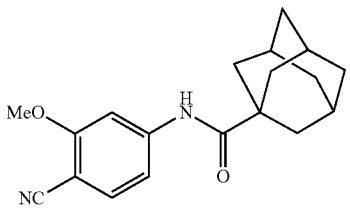

[Chemical Formula 8]

Example 1 is repeated to obtain 136 mg (yield 71%) of the target product as yellow solid, except that 3-methoxy-4-cyanoaniline is used instead of 3-methyl-4-nitroaniline. The NMR results of the product are shown below. It can be seen from the NMR results that the product is adamantan-1-carboxylic acid-(4-cyano-3-methoxy-phenyl)-amide.

$^1$H NMR (300 MHz, CDCl$_3$, δ): 7.81 (d, 1H, J=1.8 Hz), 7.50 (s, 1H), 7.43 (d, 1H, J=8.4 Hz), 6.81 (dd, 1H, J=1.5 and J=8.4 Hz), 3.93 (s, 3H), 2.11 (s, 3H), 2.00-1.88 (m, 6H), 1.82-1.71 (m, 6H).

[Example 6] Preparation of Adamantan-1-carboxylic acid-(4-cyano-2-chloro-phenyl)-amide

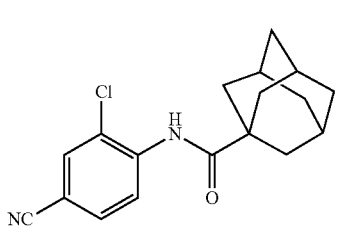

[Chemical Formula 9]

Example 1 is repeated to obtain 121 mg (yield 65%) of the target product as yellow solid, except that 2-chloro-4-cyanoaniline is used instead of 3-methyl-4-nitroaniline. The NMR results of the product are shown below. It can be seen from the NMR results that the product is adamantan-1-carboxylic acid-(4-cyano-2-chloro-phenyl)-amide.

$^1$H NMR (300 MHz, CDCl$_3$, δ): 8.65 (d, 1H, J=8.7 Hz), 8.19 (s, 1H), 7.66 (d, 1H, J=1.5 Hz), 7.55 (dd, 1H, J=1.5 and J=8.7 Hz), 2.13 (s, 3H), 2.19-1.88 (m, 6H), 1.83-1.72 (m, 6H).

[Example 7] Preparation of N-adamantan-1-yl-N-(4-nitro-3-methyl-phenyl)-acetamide

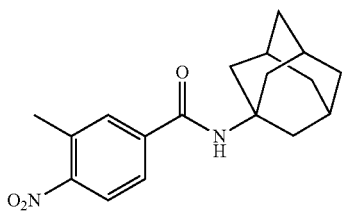

[Chemical Formula 10]

Adamantanamine (100 mg, 0.66 mmol, 1.1 eq) is dissolved into pyridine (1 ml). Next, 3-methyl-4-nitrobenzoyl chloride (100 mg, 0.60 mmol, 1.0 eq) is added gradually thereto at 0° C. The reaction mixture is agitated at room temperature for 3 hours. The reaction mixture is introduced to and diluted with ethyl acetate. Then, the reaction mixture is washed with 1N aqueous hydrochloric acid twice. After that, the reaction mixture is washed with saline, dried over dry manganese (100 mg), filtered, concentrated and separated by column chromatography to obtain 153 mg of the target product (yield 81%). The NMR results of the product are shown below. It can be seen from the NMR results that the product is N-adamantan-1-yl-N-(4-nitro-3-methyl-phenyl)-acetamide.

$^1$H NMR (300 MHz, CDCl$_3$, δ): 7.96 (d, 1H, J=8.4 Hz), 7.68 (s, 1H), 7.18 (d, 1H, J=8.4 Hz), 5.79 (s, 1H), 2.62 (s, 3H), 2.13 (s, 9H), 1.73 (s, 6H).

[Example 8] Preparation of N-adamantan-1-yl-N-(4-nitro-3-methoxy-phenyl)-acetamide

[Chemical Formula 11]

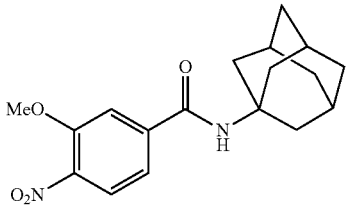

Example 7 is repeated to obtain 161 mg (yield 81%) of the target product, except that 3-methoxy-4-nitrobenzoyl chloride is used instead of 3-methyl-4-nitrobenzoyl chloride. The NMR results of the product are shown below. It can be seen from the NMR results that the product is N-adamantan-1-yl-N-(4-nitro-3-methoxy-phenyl)-acetamide.

$^1$H NMR (DMSO-d$_6$, δ): 7.82 (d, 1H, J=8.4 Hz), 7.75 (s, 1H), 7.18 (dd, 1H, J=1.2 and J=8.1 Hz), 5.83 (s, 1H), 4.00 (s, 3H), 2.13 (s, 9H), 1.73 (s, 6H).

[Example 9] Preparation of N-adamantan-1-yl-N-(4-nitro-3-chloro-phenyl)-acetamide

[Chemical Formula 12]

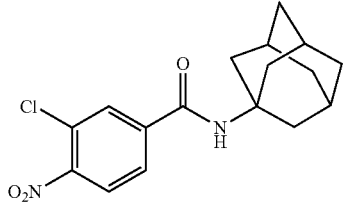

Example 7 is repeated to obtain 167 mg (yield 83%) of the target product, except that 3-chloro-4-nitrobenzoyl chloride is used instead of 3-methyl-4-nitrobenzoyl chloride. The NMR results of the product are shown below. It can be seen from the NMR results that the product is N-adamantan-1-yl-N-(4-nitro-3-chloro-phenyl)-acetamide.

$^1$H NMR (300 MHz, CDCl$_3$, δ): 8.24 (d, 1H, J=2.1 Hz), 8.13 (dd, 1H, J=1.2 and J=8.7 Hz), 7.71 (d, 1H, J=8.7 Hz), 5.70 (s, 1H), 2.13 (s, 9H), 1.73 (s, 6H).

[Example 10] Preparation of N-adamantan-1-yl-N-(4-nitro-2-chloro-phenyl)-acetamide

[Chemical Formula 13]

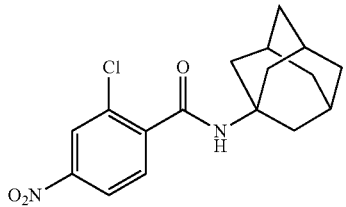

Example 7 is repeated to obtain 106 mg (yield 53%) of the target product, except that 2-chloro-4-nitrobenzoyl chloride is used instead of 3-methyl-4-nitrobenzoyl chloride. The NMR results of the product are shown below. It can be seen from the NMR results that the product is N-adamantan-1-yl-N-(4-nitro-2-chloro-phenyl)-acetamide.

$^1$H NMR (300 MHz, CDCl$_3$, δ): 7.87 (d, 1H, J=2.1 Hz), 7.87 (s, 1H), 7.70 (dd, 1H, J=1.2 and J=8.4 Hz), 5.78 (s, 1H), 2.11 (s, 9H), 1.73 (s, 6H).

[Example 11] Preparation of Adamantan-1-carboxylic Acid benzo[1,3]dioxol-5-ylamide

[Chemical Formula 14]

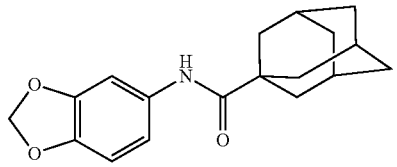

First, 3,4-methylenedioxyaniline (890 mg, 6.5 mmol) is dissolved into chloroform (50 ml), triethylamine (0.9 ml, 6.5 mmol) is added to the resultant solution and 1-adamantan-carboxyl chloride (1.19 g, 5.9 mmol) is added gradually dropwise thereto. The reaction mixture is agitated at room temperature for 2 hours. Then, the reaction mixture is washed with 1N aqueous hydrochloric acid twice. After that, the reaction mixture is washed with saline, dried over dry magnesium sulfate, filtered, concentrated and separated by column chromatography to obtain 770 mg of the target product (yield 40%). The NMR results of the product are shown below. It can be seen from the NMR results that the product is adamantan-1-carboxylic acid benzo[1,3]-dioxol-5-ylamide.

$^1$H NMR (300 MHz, DMSO-d$_6$, δ): 8.19 (s, 1H), 7.31 (d, 1H, J=1.8 Hz), 7.06-7.03 (m, 1H), 6.82-6.80 (m, 1H), 5.95 (s, 2H), 2.00 (s, 3H), 1.87 (s, 6H), 1.69 (s, 6H).

[Example 12] Preparation of Adamantan-1-carboxylic Acid benzothiazol-6-ylamide

[Chemical Formula 15]

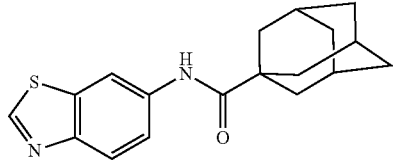

Example 11 is repeated to obtain 1.54 g (yield 76%) of the target product as white solid, except that 6-aminobenzothiazole is used instead of 3,4-methylenedioxyaniline. The NMR results of the product are shown below. It can be seen from the NMR results that the product is adamantan-1-carboxylic acid benzothiazol-6-ylamide.

$^1$H NMR (300 MHz, DMSO-d$_6$, δ): 9.36 (s, 1H), 9.24 (s, 1H), 8.55 (d, 1H, J=1.8 Hz), 8.00-7.97 (m, 1H), 7.72-7.68 (m, 1H), 2.03 (s, 3H), 1.94 (s, 6H), 1.71 (s, 6H).

[Example 13] Preparation of Adamantan-1-carboxylic Acid (3-methoxyphenyl)amide

[Chemical Formula 16]

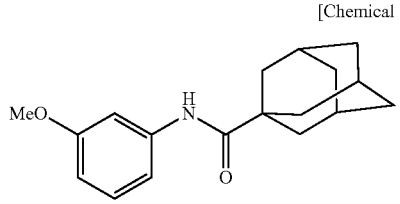

Example 11 is repeated to obtain 1.04 g (yield 56%) of the target product as white solid, except that 3-methoxyaniline is used instead of 3,4-methylenedioxyaniline. The NMR results of the product are shown below. It can be seen from the NMR results that the product is adamantan-1-carboxylic acid (3-methoxyphenyl)amide.

$^1$H NMR (300 MHz, DMSO-$d_6$, δ): 9.04 (s, 1H), 7.35-7.13 (m, 3H), 6.61-6.58 (m, 1H), 3.71 (s, 3H), 2.01 (s, 3H), 1.89 (s, 6H), 1.70 (s, 6H).

[Example 14] Preparation of Adamantan-1-carboxylic Acid (4-nitrophenyl)amide

[Chemical Formula 17]

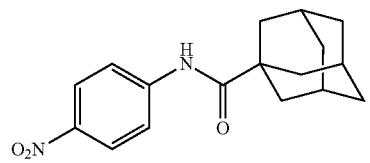

Example 11 is repeated to obtain 0.85 g (yield 44%) of the target product as white solid, except that 4-nitroaniline is used instead of 3,4-methylenedioxyaniline. The NMR results of the product are shown below. It can be seen from the NMR results that the product is adamantan-1-carboxylic acid (4-nitrophenyl)amide.

$^1$H NMR (300 MHz, DMSO-$d_6$, δ): 9.70 (s, 1H), 8.19 (m, 2H), 7.95 (m, 2H), 2.02 (s, 3H), 1.92 (s, 6H), 1.70 (s, 6H).

[Example 15] Preparation of Adamantan-1-carboxylic Acid phenylamide

[Chemical Formula 18]

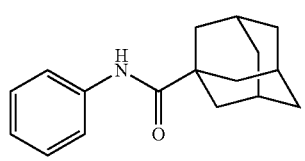

Example 11 is repeated to obtain 1.25 g (yield 75%) of the target product as white solid, except that aniline is used instead of 3,4-methylenedioxyaniline. The NMR results of the product are shown below. It can be seen from the NMR results that the product is adamantan-1-carboxylic acid phenylamide.

$^1$H NMR (300 MHz, DMSO-$d_6$, δ): 9.08 (s, 1H), 7.65-7.63 (m, 2H), 7.27 (m, 2H), 7.02 (m, 1H), 2.01 (s, 3H), 1.90 (s, 6H), 1.70 (s, 6H).

[Example 16] Preparation of Adamantan-1-carboxylic Acid (3,4-dimethoxyphenyl)amide

[Chemical Formula 19]

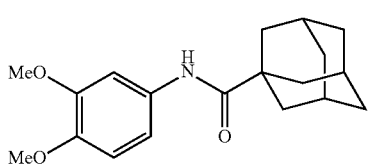

Example 11 is repeated to obtain 1.62 g (yield 79%) of the target product as white solid, except that 3,4-dimethoxyaniline is used instead of 3,4-methylenedioxyaniline. The NMR results of the product are shown below. It can be seen from the NMR results that the product is adamantan-1-carboxylic acid (3,4-dimethoxyphenyl)amide.

$^1$H NMR (300 MHz, DMSO-$d_6$, δ): 8.93 (s, 1H), 7.33 (s, 1H), 7.22-7.19 (m, 1H), 6.86-6.83 (m, 1H), 3.71 (s, 3H), 2.00 (s, 3H), 1.88 (s, 6H), 1.70 (s, 6H).

[Example 17] Preparation of Adamantan-1-carboxylic Acid (4-fluoro-3-methoxyphenyl)amide

[Chemical Formula 20]

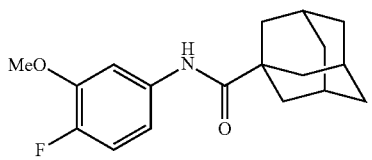

Example 11 is repeated to obtain 1.16 g (yield 59%) of the target product as white solid, except that 4-fluoro-3-methoxyaniline is used instead of 3,4-methylenedioxyaniline. The NMR results of the product are shown below. It can be seen from the NMR results that the product is adamantan-1-carboxylic acid (4-fluoro-3-methoxyphenyl)amide.

$^1$H NMR (300 MHz, DMSO-$d_6$, δ): 9.13 (s, 1H), 7.56-7.54 (m, 1H), 7.25 (m, 1H), 7.13-7.07 (m, 1H), 3.80 (s, 3H), 2.01 (s, 3H), 1.89 (s, 6H), 1.70 (s, 6H).

[Example 18] Preparation of Adamantan-1-carboxylic Acid benzoxazol-6-ylamide

[Chemical Formula 21]

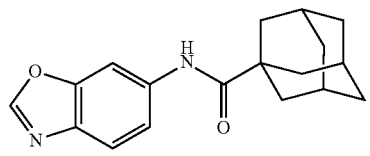

Example 11 is repeated to obtain 0.47 g (yield 24%) of the target product as brown solid, except that 6-aminobenzoxazole is used instead of 3,4-methylenedioxyaniline. The NMR results of the product are shown below. It can be seen from the NMR results that the product is adamantan-1-carboxylic acid benzoxazol-6-ylamide.

$^1$H NMR (300 MHz, DMSO-d$_6$, δ): 9.37 (s, 1H), 8.64 (s, 1H), 8.24 (s, 1H), 7.71-7.68 (m, 1H), 7.59-7.56 (m, 1H), 2.03 (s, 3H), 1.93 (s, 6H), 1.72 (s, 6H).

[Example 19] Preparation of Adamantan-1-carboxylic Acid (4-bromo-3-methoxyphenyl)amide

[Chemical Formula 22]

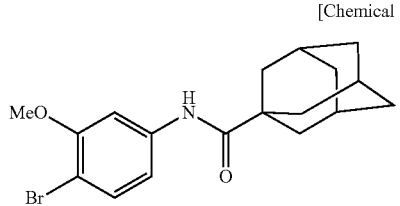

Example 11 is repeated to obtain 1.28 g (yield 54%) of the target product as white solid, except that 4-bromo-3-methoxyaniline is used instead of 3,4-methylenedioxyaniline. The NMR results of the product are shown below. It can be seen from the NMR results that the product is adamantan-1-carboxylic acid (4-bromo-3-methoxyphenyl)amide.

$^1$H NMR (300 MHz, DMSO-d$_6$, δ): 9.22 (s, 1H), 7.55 (s, 1H), 7.45~7.43 (m, 1H), 7.32~7.29 (m, 1H), 3.81 (s, 3H), 2.02 (s, 3H), 1.90 (s, 6H), 1.70 (s, 6H).

[Example 20] Preparation of Adamantan-1-carboxylic Acid quinolin-6-ylamide

[Chemical Formula 23]

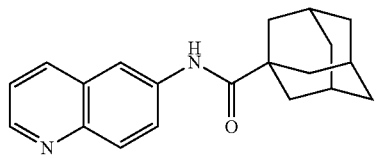

Example 11 is repeated to obtain 0.4 g (yield 20%) of the target product as yellow solid, except that 6-aminoquinoline is used instead of 3,4-methylenedioxyaniline. The NMR results of the product are shown below. It can be seen from the NMR results that the product is adamantan-1-carboxylic acid quinolin-6-ylamide.

$^1$H NMR (300 MHz, DMSO-d$_6$, δ): 9.76 (s, 1H), 9.04 (s, 1H), 8.83 (m, 1H), 8.70 (s, 1H), 8.20-8.18 (m, 2H), 7.86-7.84 (m, 1H), 2.05 (s, 3H), 1.97 (s, 6H), 1.73 (s, 6H).

[Example 21] Preparation of 4-[(adamantan-1-carbonyl)-amino]-2-methoxybenzoic Acid methylester

[Chemical Formula 24]

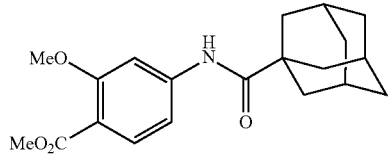

Example 11 is repeated to obtain 1.23 g (yield 55%) of the target product as white solid, except that 3-methoxy-4-methoxycarbonylaniline is used instead of 3,4-methylenedioxyaniline. The NMR results of the product are shown below. It can be seen from the NMR results that the product is 4-[(adamantan-1-carbonyl)-amino]-2-methoxybenzoic acid methylester.

$^1$H NMR (300 MHz, DMSO-d$_6$, δ): 9.36 (s, 1H), 7.67-7.59 (m, 2H), 7.43-7.40 (m, 1H), 3.78 (s, 3H), 3.74 (s, 3H), 2.02 (s, 3H), 1.91 (s, 6H), 1.71 (s, 6H).

[Example 22] Preparation of Adamantan-1-carboxylic Acid (4-methoxyphenyl)amide

[Chemical Formula 25]

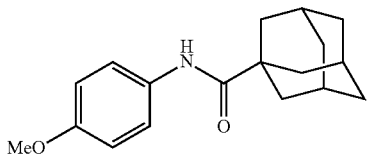

Example 11 is repeated to obtain 1.04 g (yield 56%) of the target product as purple solid, except that 4-methoxyaniline is used instead of 3,4-methylenedioxyaniline. The NMR results of the product are shown below. It can be seen from the NMR results that the product is adamantan-1-carboxylic acid (4-methoxyphenyl)amide.

$^1$H NMR (300 MHz, DMSO-d$_6$, δ): 8.96 (s, 1H), 7.52-7.51 (m, 2H), 6.85-6.83 (m, 2H), 3.71 (s, 3H), 2.00 (s, 3H), 1.88 (s, 6H), 1.69 (s, 6H).

[Example 23] Preparation of Adamantan-1-carboxylic Acid (3-nitrophenyl)amide

[Chemical Formula 26]

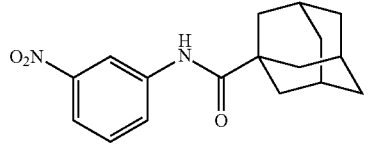

Example 11 is repeated to obtain 1.09 g (yield 56%) of the target product as white solid, except that 3-nitroaniline is used instead of 3,4-methylenedioxyaniline. The NMR results of the product are shown below. It can be seen from the NMR results that the product is adamantan-1-carboxylic acid (3-nitrophenyl)amide.

$^1$H NMR (300 MHz, DMSO-d$_6$, δ): 9.61 (s, 1H), 8.68 (s, 1H), 8.13-8.10 (m, 1H), 7.90-7.87 (m, 1H), 7.61-7.56 (m, 1H), 2.03 (s, 3H), 1.92 (s, 6H), 1.71 (s, 6H).

[Example 24] Preparation of Adamantan-1-carboxylic Acid (5,6,7,8-tetrahydronaphthalen-2-yl)amide

[Chemical Formula 27]

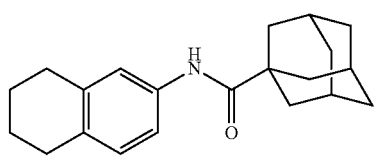

Example 11 is repeated to obtain 0.82 g (yield 41%) of the target product as white solid, except that 5,6,7,8-tetrahydronaphthylamine is used instead of 3,4-methylenedioxyaniline. The NMR results of the product are shown below. It can be seen from the NMR results that the product is adamantan-1-carboxylic acid (5,6,7,8-tetrahydronaphthalen-2-yl)amide.

$^1$H NMR (300 MHz, DMSO-d$_6$, δ): 8.93 (s, 1H), 7.34-7.31 (m, 2H), 6.95-6.92 (m, 1H), 2.64 (m, 4H), 2.00 (s, 3H), 1.88 (s, 6H), 1.70 (m, 10H).

[Example 25] Preparation of Adamantan-1-carboxylic Acid (2-methoxy-4-nitrophenyl)amide

[Chemical Formula 28]

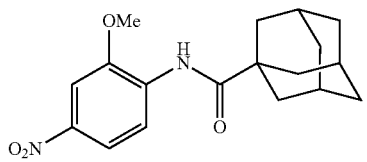

Example 11 is repeated to obtain 1.53 g (yield 90%) of the target product as yellow solid, except that 2-methoxy-4-nitroaniline is used instead of 3,4-methylenedioxyaniline. The NMR results of the product are shown below. It can be seen from the NMR results that the product is adamantan-1-carboxylic acid (2-methoxy-4-nitrophenyl)amide.

$^1$H NMR (300 MHz, DMSO-d$_6$, δ): 8.60 (s, 1H), 8.32-7.84 (m, 2H), 4.02 (s, 3H), 2.03 (s, 3H), 1.92 (s, 6H), 1.71 (s, 6H).

[Example 26] Preparation of 4-[(adamantan-1-carbonyl)-amino]-2-methoxybenzoic Acid

[Chemical Formula 29]

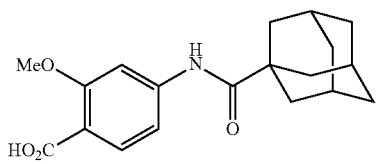

4-[(adamantan-1-carbonyl)-amino]-2-methoxybenzoic acid methylester (0.73 g) obtained from Example 22 is dissolved into methyl alcohol (20 ml) and potassium hydroxide (0.5 g) is added thereto, followed by agitation for 12 hours. After the completion of the reaction, the reaction mixture is acidified with diluted hydrochloric acid solution, extracted with dichloromethane, dried and subjected to recrystallization (dichloromethane/hexane) to obtain 0.56 g of the target product (yield 81%). The NMR results of the product are shown below. It can be seen from the NMR results that the product is 4-[(adamantan-1-carbonyl)-amino]-2-methoxybenzoic acid.

$^1$H NMR (300 MHz, DMSO-d$_6$, δ): 12.2 (brs, 1H), 9.34 (s, 1H), 7.67-7.38 (m, 3H), 3.79 (s, 3H), 2.02 (s, 3H), 1.91 (s, 6H), 1.70 (s, 6H).

[Comparative Example 1] Adamantan-1-carboxylic acid-(4-cyano-3-trifluoro-phenyl)amide First, 100 g of 1-adamantane carboxylate is dissolved into 800 ml of dichloromethane. Next, 80 g (0.79 mol) of triethylamine is added thereto, followed by reflux for 5 minutes. Then, 154 g (0.66 mol) of 4-cyano-3-trifluoromethylbenzamine is added dropwise thereto, followed by reflux at 40° C. for 2 hours. After the completion of the reaction, the reaction mixture is washed with 1000 ml of water and then with 500 ml of 0.1M HCl solution. Then, the resultant product is dried with anhydrous manganese (100 g), filtered, concentrated, crystallized with hexane, and filtered again to obtain 168 g (yield 73%) of the target product as white solid.

TLC (ethyl acetate:hexane=1:1) R$_f$=0.64. $^1$H NMR (DMSO-d$_6$, δ): 8.29 (s, 1H), 8.01 (s, 1H), 7.82 (d, 1H), 7.42 (d, 1H), 1.66-1.56 (m, 6H), 1.40-1.20 (m, 9H).

[Test Example 1] Evaluation for Anti-Androgenic Effect

To determine whether the adamantane derivative according to the present disclosure has an anti-androgenic effect or not, competitive steroid binding assay is carried out. This assay determines whether or not the adamantane derivative according to the present disclosure is bound to androgen receptor (AR) competitively with methyltrienolone, which is an agonist to androgen receptor.

Such competitive steroid binding assay is carried out by introducing tritium-labeled methyltrienolone as a ligand for androgen receptor, introducing test samples non-labeled with radio isotope thereto at a different concentration, and checking whether or not the test samples are bound to androgen receptor competitively with the ligand, methyltrienolone. In this manner, the test samples are evaluated for their anti-androgenic effects. Herein, the level of the remaining isotope, tritium, is measured to determine whether or not the test samples are bound to androgen receptor competitively with the ligand, methyltrienolone.

Particularly, wild type androgen receptor (AR) is obtained by isolating cytoplasm fraction from LNCaP cell line (ATCC® CRL-1740™). Then, competitive steroid binding assay is performed by excluding non-specific binding with 1 μM mibolerone non-labeled with isotope, and treating the androgen receptor with each of 1 nm of isotope-labeled [$^3$H] methyltrienolone, 0.1 μM-30 μM of flutamide, the adamantane derivatives according to Examples 1-10, Example 17, Example 19, Example 23 and Example 25, and the compound according to Comparative Example 1. The reaction is carried out at 4° C. for 24 hours and the reaction mixture is filtered and washed. Then, radio activity is measured in each ligand bound to the receptor. The following Table 1 shows the concentration where about 50% of the binding of methyltrienolone is inhibited in the androgen receptor.

TABLE 1

| Test samples | Concentration where about 50% of binding of methyltrienolone is inhibited in AR (IC$_{50}$) |
|---|---|
| Mibolerone | 2.6 nM |
| flutamide | 9.07 μM |
| Example 1 | 1.2 μM |
| Example 2 | 0.24 μM |
| Example 3 | 0.44 μM |
| Example 4 | 1.4 μM |
| Example 5 | 2.2 μM |
| Example 6 | 2.4 μM |
| Example 7 | 1.9 μM |
| Example 8 | 0.74 μM |
| Example 9 | 3.2 μM |
| Example 10 | 0.92 μM |
| Example 17 | 14.8 μM |
| Example 19 | 5.3 μM |
| Example 23 | 13.5 μM |
| Example 25 | 1.2 μM |
| Comp. Ex. 1 | 11.4 uM |

As can be seen from the above results, each of the compounds according to Examples 1-26 shows binding in a similar manner to flutamide known as an excellent antagonist against androgen receptor, and thus similarly inhibits the binding of methyltrienolone to androgen receptor. In addition, the adamantane derivatives according to the present disclosure are bound to androgen receptor and are more effective for inhibiting androgen activity as compared to flutamide.

[Test Example 2] Evaluation for Effect of Stimulating Growth of Dermal Papilla Cells Rat-derived follicle dermal papilla cells cultured in Dulbecco's modified Eagle's media (DMEM) containing 2% of fetal bovine serum are dispensed to a 96-well microtiter plate to 1,000 cells/well. As positive control, minoxidil diluted to a concentration of 10 μg/ml is added. Each of the adamantane derivatives according to Examples 1-10 diluted to a concentration of 10 μg/ml is added, followed by culturing at 37° C. for 48 hours. After culturing, 0.2% 3-[4,5-dimethylthiazol-2-yl]-2,5-diphenyltetrazolium bromide (MTT) solution is added to each well in an amount of 50 μl, followed by culturing at 37° C. for 4 hours. Then, the produced formazane is dissolved with dimethyl sulfoxide (DMSO). A microplate reader is used to determine the absorbance of the dissolved formazane at 570 nm. The absorbance is compared with the absorbance of control treated with DMSO solution alone and the ratio (%) of growth of dermal papilla cells is evaluated based on the relative difference. The results are shown in the following Table 2.

TABLE 2

| Treatment group | Ratio (%) of growth of dermal papilla cells |
|---|---|
| DMSO | 100 |
| minoxidil | 120 |
| Example 1 | 124 |
| Example 2 | 124 |
| Example 3 | 118 |
| Example 4 | 130 |

TABLE 2-continued

| Treatment group | Ratio (%) of growth of dermal papilla cells |
|---|---|
| Example 5 | 145 |
| Example 6 | 124 |
| Example 7 | 123 |
| Example 8 | 125 |
| Example 9 | 128 |
| Example 10 | 123 |
| Comp. Ex. 1 | 114 |

As can be seen from the above results, the compounds according to Examples 1-10 provide a higher ratio (%) of growth of dermal papilla cells as compared to minoxidil known to stimulate hair growth as well as the control treated with DMSO solution alone. This suggests that the adamantane derivatives according to the present disclosure stimulate the growth of dermal papilla cells, thereby stimulating hair growth and preventing alopecia.

[Test Example 3] Evaluation for Effect of Stimulating Hair Growth

To evaluate the adamantane derivatives according to the present disclosure for the effect of stimulating hair growth, each of the adamantane derivatives according to Examples 1-10 is dissolved into a solvent including water/ethanol/1,3-butylene glycol (5/3/2) to a concentration of 1.0 wt %. Next, mice 47-53 days after the birth are dehaired on their backs. Then, mice whose skins on the back portions are clear are selected and grouped by 8 mice per group. Each adamantane derivative having a concentration of 1.0 wt % is applied to each mouse every day in an amount of 150 μl/day for 21 days. After 21 days, newly grown hair is weighed and the weight is compared with negative control. The results are shown in the following Table 3.

TABLE 3

| Treatment group | Hair weight (mg) |
|---|---|
| Negative control | 40 ± 18 |
| Comp. Ex. 1 | 59 ± 12 |
| Example 1 | 77 ± 11 |
| Example 2 | 74 ± 9 |
| Example 3 | 72 ± 6 |
| Example 4 | 75 ± 10 |
| Example 5 | 71 ± 14 |
| Example 6 | 67 ± 12 |
| Example 7 | 68 ± 8 |
| Example 8 | 70 ± 14 |
| Example 9 | 66 ± 12 |
| Example 10 | 68 ± 8 |

As can be seen from the above results, the test groups to which the adamantane derivatives according to Examples 1-10 are applied show a higher value of hair weight as compared to the group to which the conventional solution (water/ethanol/1,3-butylene glycol) is applied. This suggests that application of each of Examples 1-10 stimulates hair growth. In other words, it can be seen that the adamantane derivatives according to the present disclosure stimulate a shift from the telogen to the anagen in hair of mice, and thus stimulates hair growth.

[Test Example 4] Evaluation for Effect of Inhibiting Secretion of Sebum

The following test is carried out to evaluate the adamantane derivatives according to Examples 1-10 for the effect of inhibiting secretion of sebum. Twenty male and female subjects suffering from excessive secretion of sebum are selected and allowed to apply nourishing cream including each of Examples 1-10 and nourishing cream of negative control every day at a predetermined site for 4 weeks. Then, Sebumeter SM810 (C&K Electronic Co., Germany) is used to determine the average ratio (%) of decrease in sebum after 2 weeks and 4 weeks. The results are shown in the following Table 4.

TABLE 4

| Test material | Ratio (%) of decrease in sebum | |
|---|---|---|
| | After 2 weeks | After 4 weeks |
| Negative control | 5 | 5 |
| Example 1 | 21.5 | 35.2 |
| Example 2 | 19.4 | 28.8 |
| Example 3 | 18.1 | 27.6 |
| Example 4 | 20.7 | 29.7 |
| Example 5 | 18.7 | 32.8 |
| Example 6 | 17.4 | 31.4 |
| Example 7 | 18.1 | 29.8 |
| Example 8 | 19.8 | 33.7 |
| Example 9 | 17.1 | 29.8 |
| Example 10 | 19.8 | 31.7 |
| Comp. Ex. 1 | 16.5 | 26.2 |

As can be seen from the above results, application of cream including each of Examples 1-10 decreases secretion of sebum. It can be seen from the above results that the adamantane derivatives according to the present disclosure are effective for inhibiting excessive secretion of sebum.

Hereinafter, some formulation examples of the composition including the adamantane derivative compound according to an aspect of the present disclosure, an isomer thereof, pharmaceutically acceptable salt thereof, prodrug thereof, hydrate thereof or a solvate thereof will be described in detail. However, the composition may be formulated in various forms and the following formulation examples are for illustrative purposes only and not intended to limit the scope of the present disclosure.

[Formulation Example 1] Preparation of Hair Nourishing Skin (Milk Lotion)

Hair nourishing skin is prepared by using the composition of the following Table 5 according to the conventional method.

TABLE 5

| Ingredients | Amount (wt %) |
|---|---|
| Purified water | Balance |
| Glycerin | 8.0 |
| Butylene glycol | 4.0 |
| Hyaluronic acid extract | 5.0 |
| Betaglucan | 7.0 |
| Carbomer | 0.1 |
| Adamantane derivative compound according to each Example | 1.0 |
| Caprylic capric triglyceride | 8.0 |
| Squalene | 5.0 |
| Cetearyl glucoside | 1.5 |
| Sorbitan stearate | 0.4 |
| Cetearyl alcohol | 1.0 |
| Preservative | Qsad |
| Fragrance | Qsad |
| Colorant | Qsad |
| Triethanolamine | 0.1 |

[Formulation Example 2] Preparation of Hair Lotion

Hair lotion is prepared by using the composition of the following Table 6 according to the conventional method.

TABLE 6

| Ingredients | Amount (wt %) |
|---|---|
| Purified water | Balance |
| Glycerin | 3.0 |
| Butylene glycol | 3.0 |
| Liquid paraffin | 7.0 |
| Betaglucan | 7.0 |
| Carbomer | 0.1 |
| Adamantane derivative compound according to each Example | 2.0 |
| Caprylic capric triglyceride | 3.0 |
| Squalene | 5.0 |
| Cetearyl glucoside | 1.5 |
| Sorbitan stearate | 0.4 |
| Polysorbate | 1.2 |
| Preservative | Qsad |
| Fragrance | Qsad |
| Colorant | Qsad |
| Triethanolamine | 0.1 |

[Formulation Example 3] Preparation of Hair Cream

Hair cream is prepared by using the composition of the following Table 7 according to the conventional method.

TABLE 7

| Ingredients | Amount (wt %) |
|---|---|
| Purified water | Balance |
| Glycerin | 8.0 |
| Butylene glycol | 4.0 |
| Liquid paraffin | 45.0 |
| Betaglucan | 7.0 |
| Carbomer | 0.1 |
| Adamantane derivative compound according to each Example | 1.5 |
| Caprylic capric triglyceride | 3.0 |
| Beeswax | 4.0 |
| Cetearyl glucoside | 1.5 |
| Sorbitan sesquioleate | 0.9 |
| Vaseline | 3.0 |
| Preservative | Qsad |
| Fragrance | Qsad |
| Colorant | Qsad |
| Triethanolamine | 0.1 |

[Formulation Example 4] Preparation of Ointment

Ointment is prepared by using the composition of the following Table 8 according to the conventional method.

TABLE 8

| Ingredients | Amount (wt %) |
|---|---|
| Purified water | Balance |
| Glycerin | 8.0 |
| Butylene glycol | 4.0 |
| Liquid paraffin | 15.0 |
| Betaglucan | 7.0 |
| Carbomer | 0.1 |
| Adamantane derivative compound according to each Example | 0.5 |

TABLE 8-continued

| Ingredients | Amount (wt %) |
| --- | --- |
| Caprylic capric triglyceride | 3.0 |
| Squalene | 1.0 |
| Cetearyl glucoside | 1.5 |
| Sorbitan stearate | 0.4 |
| Stearyl alcohol | 1.0 |
| Preservative | Qsad |
| Fragrance | Qsad |
| Colorant | Qsad |
| Beeswax | 4.1 |

The invention claimed is:

1. A compound represented by the following Chemical Formula 1, an isomer thereof, pharmaceutically acceptable salt thereof, prodrug thereof, hydrate thereof or a solvate thereof:

[Chemical Formula 1]

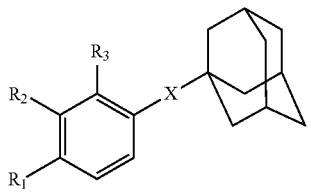

wherein X is —NHCO— or —CONH—, each of $R_1$ and $R_2$ is independently substituted, $R_1$ is selected from the group consisting of hydrogen, halogen, $NO_2$, $C_1$-$C_6$ alkoxy, CN, $CO_2Me$, $CO_2H$ and $NH_2$, $R_2$ is selected from the group consisting of hydrogen, $C_1$-$C_6$ alkoxy, $C_1$-$C_6$ alkyl and halogen, or $R_1$ and $R_2$ are linked to each other to form a cyclic carbon chain optionally containing a hetero atom, wherein the cyclic carbon chain is selected from the group consisting of $C_2$-$C_{18}$ cycloalkyl; $C_4$-$C_{18}$ aryl; $C_2$-$C_{18}$ heterocycloalkyl in which at least one carbon is substituted with at least one hetero atom selected from nitrogen, oxygen and sulfur; and $C_4$-$C_{18}$ heteroaryl in which at least one carbon is substituted with at least one hetero atom selected from nitrogen, oxygen and sulfur;

$R_3$ is selected from the group consisting of hydrogen, $C_1$-$C_6$ alkoxy and halogen, wherein the compound is selected from the group consisting of:

adamantan-1-carboxylic acid-(3-methyl-4-nitrophenyl) amide;
adamantan-1-carboxylic acid-(3-methoxy-4-nitrophenyl) amide;
adamantan-1-carboxylic acid-(3-chloro-4-nitrophenyl) amide;
adamantan-1-carboxylic acid-(4-cyano-3-methoxy-phenyl)amide;
adamantan-1-carboxylic acid-(4-cyano-2-chloro-phenyl) amide;
N-adamantan-1-yl-N-(4-nitro-3-methoxy-phenyl)-acetamide,
N-adamantan-1-yl-N-(4-nitro-3-chloro-phenyl)-acetamide,
adamantan-1-carboxylic acid (4-fluoro-3-methoxyphenyl)amide;
adamantan-1-carboxylic acid benzoxazol-6-yl amide;
adamantan-1-carboxylic acid (4-bromo-3-methoxyphenyl)amide;
4-[(adamantan-1-carbonyl)-amino]2-methoxy-benzoic acid methylester;
adamantan-1-carboxylic acid (5,6,7,8-tetrahydronaphthalen-2-yl)amide;
and
4-[(adamantan-1-carbonyl)-amino]-2-methoxybenzoic acid.

2. The compound according to claim 1 which is adamantan-1-carboxylic acid-(3-methoxy-4-nitrophenyl)amide.

3. A method for inhibiting androgen of a subject, wherein the method comprises administering an effective amount of the compound, isomer thereof, pharmaceutically acceptable salt thereof, prodrug thereof, hydrate thereof or solvate thereof according to claim 1 to the subject in need thereof.

4. The method according to claim 3, wherein the compound, isomer thereof, pharmaceutically acceptable salt thereof, prodrug thereof, hydrate thereof or solvate thereof, stimulates hair growth.

5. The method according to claim 3, wherein the compound, isomer thereof, pharmaceutically acceptable salt thereof, prodrug thereof, hydrate thereof or solvate thereof, inhibits sebum production.

6. A composition comprising the compound, isomer thereof, pharmaceutically acceptable salt thereof, prodrug thereof, hydrate thereof or solvate thereof as defined in claim 1.

7. The composition according to claim 6, which comprises the compound, isomer thereof, pharmaceutically acceptable salt thereof, prodrug thereof, hydrate thereof or solvate thereof as defined in claim 1, in an amount of 0.01 wt %-20 wt % based on the total weight of the composition.

8. The composition according to claim 6, which is a skin application composition.

9. The composition according to claim 6, which is an anti-androgenic composition.

10. The composition according to claim 6, which is a composition for stimulating hair growth.

11. The composition according to claim 6, which is an anti-sebum composition.

12. A method for preparing the compound, isomer thereof, pharmaceutically acceptable salt thereof, prodrug thereof, hydrate thereof or solvate thereof as defined in claim 1, the method comprising:

reacting a compound represented by the following Chemical Formula 2 or 3 with a benzoic acid salt derivative or phenylamine derivative in the presence of a base:

[Chemical Formula 2]

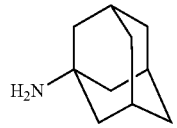

[Chemical Formula 3]

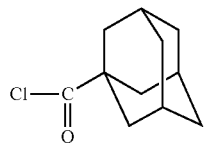

wherein the benzoic acid salt derivative is selected from the group consisting of 3-methoxy-4-nitrobenzoyl chloride, and 3-chloro-4-nitrobenzoyl chloride, and wherein the phenylamine derivative is selected from the group consisting of 3-methyl-4-nitroaniline, 3-methoxy-4-nitroaniline, 3-chloro-4-nitroaniline, 3-methoxy-4-cyanoaniline, 2-chloro-4-cyanoaniline, 6-aminobenzothiazole, 4-fluoro-3-methoxyaniline, 4-bromo-3-methoxyaniline, 3-methoxy-4-methoxycarbonylaniline, and 5,6,7,8-tetrahydronaphthylamine.

* * * * *